United States Patent [19]
Kassebaum et al.

[11] Patent Number: 5,912,209
[45] Date of Patent: Jun. 15, 1999

[54] SURFACTANTS PROVIDING ENHANCED EFFICACY AND/OR RAINFASTNESS TO GLYPHOSATE FORMULATIONS

[75] Inventors: James W. Kassebaum, Indianapolis, Ind.; Joseph J. Sandbrink, Des Peres; James M. Warner, St. Louis, both of Mo.

[73] Assignee: Monsanto Company, St. Louis, Mo.

[21] Appl. No.: 08/927,364

[22] Filed: Sep. 9, 1997

Related U.S. Application Data

[63] Continuation of application No. 08/576,268, Dec. 21, 1995, abandoned, which is a continuation of application No. 08/341,501, Nov. 22, 1994, abandoned, which is a continuation-in-part of application No. 08/169,805, Dec. 17, 1993, abandoned.

[51] Int. Cl.$^6$ .......................... A01N 25/30; A01N 25/24; A01N 57/02
[52] U.S. Cl. .................................................. 504/206
[58] Field of Search .............................. 504/206

[56] References Cited

U.S. PATENT DOCUMENTS

| | | | |
|---|---|---|---|
| 4,259,217 | 3/1981 | Murphy | 252/547 |
| 4,990,175 | 2/1991 | Petroff et al. | 71/DIG. 1 |
| 5,078,782 | 1/1992 | Nielsen et al. | 71/100 |
| 5,118,444 | 6/1992 | Nguyen | 252/390 |
| 5,258,354 | 11/1993 | Tack | 503/227 |
| 5,258,359 | 11/1993 | Kassebaum et al. | 504/206 |

FOREIGN PATENT DOCUMENTS

| | | | |
|---|---|---|---|
| B-64552/86 | 5/1987 | Australia | A01N 57/20 |
| B-38389/89 | 1/1990 | Australia | A01N 25/30 |
| 987925 | 4/1976 | Canada | 71/10.8 |
| 0 274 369 | 7/1988 | European Pat. Off. | A01N 57/20 |
| 0 290 416 | 11/1988 | European Pat. Off. | A01N 25/30 |
| 0 472 310 | 2/1992 | European Pat. Off. | A01N 25/30 |
| 0 498 785 | 8/1992 | European Pat. Off. | A01N 57/20 |
| 0 531 269 | 3/1993 | European Pat. Off. | A01N 57/20 |
| 2589328 | 5/1987 | France . | |
| 240 081 | 5/1993 | New Zealand | A01N 7/20 |
| 243 779 | 10/1993 | New Zealand . | |
| 243 780 | 12/1993 | New Zealand | A01N 7/20 |
| 243 778 | 2/1994 | New Zealand . | |

OTHER PUBLICATIONS

Satkowski et al "Properties of Polyoxyethylene Alcohols," pp. 102–111 Martin J. Schick (Ed.) "Nonionic Surfactants" 1967, Marcel Dekker, NY.
Tergitol Product Information, Union Carbide (1989).
Brumbaugh, E. H., *Third International Symposium on Adjuvants for Agrochemicals*, Cambridge, U.K., (Aug. 1992). *Abstract.
Wyrill et al. "Glyphosate Toxicity . . . as Influenced by Surfactants." *Weed Science* 25(3):275–287. May 1977.

*Primary Examiner*—S. Mark Clardy
*Attorney, Agent, or Firm*—James C. Forbes; Arnold, White & Durkee

[57] ABSTRACT

There is provided a new method of use of secondary or tertiary alcohol surfactants to enhance the efficacy and/or rainfastness of foliar-applied pesticidal and plant growth modifying agents. More specifically, there are provided new and useful compositions of such agents, in particular the herbicide N-phosphonomethylglycine or its salts or mixtures thereof, containing such efficacy-enhancing or rainfastness-enhancing surfactants.

31 Claims, No Drawings

SURFACTANTS PROVIDING ENHANCED EFFICACY AND/OR RAINFASTNESS TO GLYPHOSATE FORMULATIONS

This application is a continuation of application Ser. No. 08/576,268, filed Dec. 21, 1995, now abandoned, which is a continuation of application Ser. No. 08/341,501, filed Nov. 22, 1994, now abandoned, which is a continuation-in-part of application Ser. No. 08/169,805, filed Dec. 17, 1993, now abandoned.

FIELD OF THE INVENTION

This invention comprises a new method of use of relatively low-cost, agriculturally acceptable surfactants to enhance the rainfastness of foliar-applied pesticidal and plant growth modifying agents. This invention further comprises new and useful compositions of such agents, in particular the herbicide N-phosphonomethylglycine or its salts or mixtures thereof, containing such efficacy- or rainfastness-enhancing surfactants.

BACKGROUND OF THE INVENTION

Foliar-applied pesticidal and plant growth modifying chemicals are widely used in agricultural, industrial, recreational and residential areas worldwide. These chemical agents illustratively include insecticides, fungicides, herbicides, plant growth regulators and plant nutrients among other chemicals. Such chemicals are typically applied by spraying on the foliage of vegetation to be protected, controlled, killed or modified, but other methods such as rope-wick application are known. Some of these agents show contact action, killing, controlling or modifying the growth of target organisms at the site of deposition. Other chemicals are systemic, translocating within the plant to a site of action remote from the site of deposition. Still other chemicals show both contact and systemic action.

A common concern with several such chemicals is that efficacy can be reduced if rain falls shortly after spraying or other mode of application. This concern is more pronounced with chemicals that have moderate to high solubility in water. Many methods of overcoming the problem of reduced efficacy due to rain have been disclosed. Such methods are said to have the aim of enhancing "rainfastness" of foliar-applied agents.

Methods to enhance rainfastness include addition to the spray solution of oils or other lipophilic substances, polymers and other materials which are alleged to enhance spreading and sticking of the applied formulation to leaves, and addition of various surfactants. Among surfactants which have been disclosed for rainfastness enhancement are organosilicone copolymers, for example the ethoxylated siloxane Silwet L-77 of Union Carbide Corporation. Such surfactants, as well as other spray additives used to enhance rainfastness, tend to be relatively expensive and many have other drawbacks.

Alternatively, a rainfastness enhancing material may be provided by the manufacturer or supplier of the foliar-applied pesticidal or plant growth modifying agent as an ingredient in the formulation of said agent.

An example of a foliar-applied agent whose efficacy is sensitive to the occurrence of rain shortly after application is the herbicide N-phosphono-methylglycine, also known by its common name glyphosate.

Glyphosate is a highly effective and commercially important herbicide useful for combating the presence of a wide variety of unwanted vegetation, including agricultural weeds. Glyphosate is applied as a formulated product to the foliage of annual and perennial grasses and broadleaf plants and the like, and is taken up over a period of time into the leaves whence it translocates throughout the plant.

Glyphosate in ionic form has relatively high water solubility, especially when formulated as a salt, and during the uptake period immediately after application glyphosate is vulnerable to being washed off the foliage by rain or by overhead watering or irrigation. As glyphosate has practically no herbicidal activity in the soil, its efficacy is seriously reduced by such washing.

The length of time during which glyphosate is somewhat vulnerable to rain depends on many environmental and plant factors, and on the duration and intensity of rain, but can be as short as thirty minutes or as long as twelve hours or more after application. In the great majority of cases rain falling six or more hours after application does not seriously affect performance of the herbicide.

Usually, glyphosate is formulated in commercial compositions in the form of a water-soluble salt. Salts in commercial use include alkylamine salts, such as the isopropylamine salt, alkali metal salts, such as the sodium salt, the ammonium salt and the trimethylsulfonium salt. However, formulations of glyphosate in its acid form are also used. Typical glyphosate salt formulations include aqueous concentrates, requiring simple dilution in water for application by the end-user, and water-soluble or water-dispersible dry formulations, especially granules, requiring dissolution or dispersion in water prior to application. Most formulations, whether liquid or dry, also contain one or more surfactants. Even with such surfactants in the formulation there remains a need for enhanced rainfastness of glyphosate in many situations.

The ethoxylated siloxane surfactant Silwet L-77 referred to above has been the subject of much published research into rainfastness enhancement for glyphosate salt formulations. Its main active ingredient is 1,1,1,3,5,5,5-heptamethyltrisiloxanylpropyl-omega-methoxypoly (ethylene oxide) where the average number of ethylene oxide units is approximately seven. Other siloxanes of related composition are also described in the art. In addition to the high cost of Silwet L-77, common to all siloxanes, a number of disadvantages have been described, notably its tendency to antagonize the activity of glyphosate on some species in the absence of rain. A technical solution to this problem is provided in Australian Patent No. 609,628, wherein a humectant such as glycerin added to the spray solution overcomes the antagonism; however cost still remains a major deterrent in most situations.

A major advance in cost-effective rainfastness enhancement for glyphosate was provided in U.S Pat. No. 5,258,354, wherein acetylenic diol surfactants, exemplified by ethoxylates of 2,4,7,9-tetramethyl-5-decyne-4,7-diol, are shown to give rainfastness at least equal to Silwet L-77 when used in the presence of certain other surfactants, but without the occurrence of antagonism in the absence of rain. Concentrate formulations of glyphosate with such acetylenic diol surfactants are disclosed which are both chemically and physically stable over a wide range of conditions.

While acetylenic diol surfactants are obtainable at much lower cost than effective organosilicone surfactants, they could still be too costly for many applications. In most cases the end-user wishes some degree of insurance against the possibility of rain washing the herbicide off the foliage before it has had time to penetrate into the leaves. The end-user seldom knows that it will certainly rain. For such insurance purposes, economics dictate a still lower-cost adjuvant or formulation ingredient. Various low-cost surfactants have from time to time been claimed to give rainfastness enhancement, including ethoxylated alkylphenols such as octylphenol and nonylphenol ethoxylates. These are among the most widely used general purpose adjuvants for glyphosate in many markets, and are not considered by most users to provide reliable rainfastness enhancement.

E. H. Brumbaugh (Third International Symposium on Adjuvants for Agrochemicals, Cambridge, U.K., August 1992) showed that addition of APSA-80, a product said to contain 80% of a nonionic surfactant based on nonoxynol-9 (nonylphenol ethoxylate with an average of 9 moles ethylene oxide per mole of nonylphenol), enhanced rainfastness of glyphosate, applied as Roundup® herbicide in an ultra-low volume of water (30.6 l/ha). The adjuvant was used at concentrations ranging from 0.1% to 0.5% of the spray solution. Rainfastness improvement was not evident on all species.

There is provided herein a new method of use of secondary or tertiary alcohol alkoxylates of molecular structure defined more particularly below for enhancing the rainfastness of foliar-applied pesticidal and plant growth modifying agents.

There are also provided herein new, storage-stable, liquid or dry concentrate compositions comprising glyphosate or one or more of its salts, a secondary or tertiary alcohol alkoxylate of molecular structure defined below and one or more other surfactants, said compositions showing enhanced rainfastness by comparison with similar compositions not containing said secondary or tertiary alcohol alkoxylate, and showing at least equal rainfastness by comparison with much higher-cost compositions of the prior art based on ethoxylated siloxane or acetylenic diol surfactants. Not all alcohol alkoxylates provide the desired degree of rainfastness enhancement. Secondary or tertiary alcohol alkoxylates, when used in accordance with the present invention, have been shown to give superior rainfastness by comparison with, for example, primary alcohol alkoxylates or alkylphenol alkoxylates of the prior art.

Also provided herein are new, storage-stable, liquid or dry concentrate compositions comprising glyphosate or one or more of its salts, a secondary or tertiary alcohol alkoxylate of molecular structure defined below and one or more other surfactants, said compositions showing enhanced efficacy by comparison with glyphosate compositions known in the art, even in the absence of rain.

Wyrill and Burnside, Weed Science, Vol. 25 (1977), pp. 275–287, in a wide-ranging study of different classes of surfactant tested two secondary or tertiary alcohol ethoxylates from Union Carbide Corporation, namely Tergitol 15-S-9 and Tergitol TMN-3, in tank-mix with glyphosate. (The structure given by Wyrill and Burnside for Tergitol TMN-3 does not reveal this to be a secondary or tertiary alcohol.) When used as the sole surfactant, even at very high use rates, neither of these showed performance (in the absence of rain) comparable to the most efficacious surfactants tested. No motivation is provided to those of skill in the art to evaluate these surfactants further. No suggestion is made or implied in the art that secondary or tertiary alcohol alkoxylates could be useful for enhancement of glyphosate performance when combined with other surfactants, nor that rainfastness benefits might be obtainable with secondary or tertiary alcohol alkoxylates.

Among the surfactants used in combination with secondary or tertiary alcohol alkoxylates in compositions of the present invention are ethoxylated tertiary and quaternary alkylamines and alkylamine oxides.

It is known in the art that ethoxylated alkylamine or alkylamine oxide surfactants having an average alkyl chain length in the range from 10 to 20 carbon atoms and having an average of from 2 to 20 moles of ethylene oxide (EO) per mole of amine, are effective in potentiating the herbicidal activity of glyphosate compositions. European Patent No. 0 290 416, for example, discloses glyphosate compositions containing tertiary alkylamine surfactants within the range encompassed by the above description, and notes that such compositions, particularly those with EO levels in the lower part of the range mentioned above, have high herbicidal unit activity. European Patent No. 0 274 369 discloses highly efficacious glyphosate compositions containing quaternary alkylamine surfactants within the range encompassed by the above description. In both cases it is disclosed that for best performance the compositions should also contain a significant amount of an inorganic ammonium salt such as ammonium sulfate.

U.S. Pat. No. 5,118,444 discloses ethoxylated alkylamine oxide surfactants within the range encompassed by the above description, and indicates their usefulness as components of glyphosate formulations.

Ammonium sulfate is bulky and can only be accommodated in a concentrate formulation at an effective level by greatly lowering the content of active ingredient, in this case glyphosate. A significant advance in the art of formulating glyphosate concentrates would result from identification of a material which further enhances the efficacy of compositions containing ethoxylated alkylamine surfactants, but which is effective at a lower concentration than is required in the case of ammonium sulfate. That material could be incorporated in a concentrate formulation without unacceptable dilution of the glyphosate active ingredient. The present invention provides just such an advance in the art.

SUMMARY OF THE INVENTION

There is provided a new method, for enhancing the rainfastness of foliar-applied pesticidal and plant growth modifying agents, using secondary and tertiary alcohol surfactants such as those having the representative chemical structure

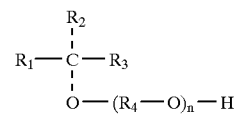

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen or a straight or branched chain $C_1$ to about $C_{28}$ alkyl, aryl or alkylaryl group, $R_4$ groups are independently $C_1$ to $C_4$ alkylene groups and n is an average number from about 3 to about 30.

There are also provided new, storage-stable, liquid or dry concentrate compositions comprising (a) glyphosate or one or more of its agriculturally acceptable salts, (b) one or more secondary or tertiary alcohol surfactants such as those having the representative chemical structure

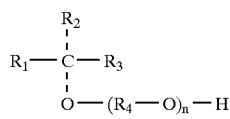

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen or a straight or branched chain $C_1$ to about $C_{28}$ alkyl, aryl or alkylaryl group, $R_4$ groups are independently $C_1$ to $C_4$ alkylene groups and n is an average number from about 3 to about 30, and (c) one or more other surfactants. In preferred compositions, $R_3$ in the structure of the alcohol surfactant is hydrogen and $R_4$ is ethylene.

Compositions of the invention possess at least one of the following benefits over compositions known in the art. (1) They may show enhanced rainfastness by comparison with similar compositions not containing said secondary or tertiary alcohol surfactants, and at least substantially equal rainfastness by comparison with much higher-cost compositions of the prior art based on ethoxylated siloxane or acetylenic diol surfactants. (2) They may show enhanced herbicidal efficacy, even in the absence of rain, by comparison with similar compositions not containing said secondary or tertiary alcohol surfactants.

A method of use of such compositions to provide acceptable control of weeds and other unwanted vegetation whether or not rain falls shortly after application is also provided.

DETAILED DESCRIPTION OF THE INVENTION

In the most widely used commercial glyphosate compositions, the herbicide glyphosate is formulated as its isopropylamine salt. Excellent control of most plant species can normally be obtained at rates of 0.1 to 10 kg/ha of glyphosate-isopropylamine. It is generally preferred to refer to the amount of glyphosate applied in terms of glyphosate acid equivalent, conventionally abbreviated as "a.e.". Application to plants is most commonly done by spraying a solution of the glyphosate herbicide in water.

For most applications, the efficacy of glyphosate is significantly improved by the presence of a surfactant. However, not all surfactants are equally effective in improving the herbicidal activity of glyphosate, and some surfactants are quite ineffective or may even reduce glyphosate activity. Among the most effective prior art surfactants for improving glyphosate activity are alkoxylated alkylamine surfactants, including both tertiary and quaternary amine types. Nonionic surfactants differ widely and to a large extent unpredictably in their ability to enhance glyphosate activity. The secondary and tertiary alcohol alkoxylates of the present invention are relatively weak in this regard, when used as the sole surfactant.

Most commercial glyphosate salt formulations already contain one or more surfactants, most commonly of the tertiary or quaternary alkylamine alkoxylate class mentioned above. For example, Roundup® herbicide of Monsanto Company is an aqueous concentrate formulation of the isopropylamine salt of glyphosate. In addition to glyphosate in the amount of 360 grams a.e./liter, Roundup herbicide as sold, for example, in the U.S. contains a surfactant based on ethoxylated tallowamine having an average of about 15 moles EO per mole of amine.

The end-user may add more surfactant to a glyphosate spray solution; as well as amines, low-cost nonionic surfactants of the ethoxylated primary alcohol, alkylphenol or fatty acid classes are especially widely used in this way. However, because of the wide variation in efficacy of such surfactants it is generally preferred to include an effective surfactant in the concentrate formulation. In addition to the relatively poor efficacy of secondary and tertiary alcohol alkoxylates when used as the sole surfactant with glyphosate, these alcohol surfactants suffer the further drawback that they cannot be formulated with glyphosate salts in agriculturally useful amounts in aqueous concentrates, except in the presence of compatibilizing agents. Such agents include a wide variety of tertiary and quaternary amine surfactants, alkyl polyglycosides and other materials.

There is now provided a new method, for enhancing the rainfastness of foliar-applied pesticidal and plant growth modifying agents, using secondary and tertiary alcohol surfactants such as those having the representative chemical structure

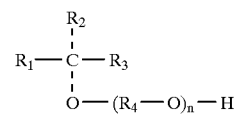

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen or a straight or branched chain $C_1$ to about $C_{28}$ alkyl, aryl or alkylaryl group, $R_4$ groups are independently $C_1$ to $C_4$ alkylene groups and n is an average number from about 3 to about 30, preferably from about 7 to about 14, and most preferably from about 9 to about 12. $R_1$ and $R_2$ are preferably straight-chain alkyl groups with a total of about 10 to about 20 carbon atoms, $R_3$ is preferably hydrogen and $R_4$ is preferably ethylene.

There are also provided new, storage-stable, liquid or dry concentrate compositions comprising (a) glyphosate or one or more of its agriculturally acceptable salts, (b) one or more secondary or tertiary alcohol surfactants such as those having the representative chemical structure

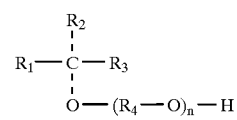

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen or a straight or branched chain $C_1$ to about $C_{28}$ alkyl, aryl or alkylaryl group, $R_4$ groups are independently $C_1$ to $C_4$ alkylene groups and n is an average number from about 3 to about 30, and (c) one or more other surfactants, said compositions showing enhanced efficacy and/or rainfastness by comparison with similar compositions not containing said secondary or tertiary alcohol surfactants, and showing at least substantially equal rainfastness by comparison with much higher-cost compositions of the prior art based on ethoxylated siloxane or acetylenic diol surfactants.

A method of use of such compositions to provide acceptable control of weeds and other unwanted vegetation whether or not rain falls shortly after application is also provided.

A particular embodiment of this invention is a surfactant composition comprising (a) an alcohol surfactant in which $R_3$ is hydrogen, $R_1$ and $R_2$ are straight chain alkyl groups with a total of about 10 to about 20 carbon atoms, $R_4$ is ethylene and n is an average number in the range from about 7 to about 14, most preferably from about 9 to about 12; and (b) an ethoxylated tertiary or quaternary alkylamine or alkylamine oxide surfactant having an average of from about 2 to about 20 moles of ethylene oxide per mole of amine. Said surfactant composition may be coformulated with a glyphosate herbicide in an aqueous or dry concentrate formulation. Alternatively, said surfactant composition may be provided to the end user separately from the glyphosate herbicide, for tank mixing by him immediately prior to application.

Typically in commercial preparations of secondary alcohol surfactants the ethoxylated alcohol group can be located anywhere on the alkyl chain except at the ends, and such preparations are therefore mixtures of alcohols. The alkyl chain length also normally varies within commercial preparations.

In the examples that follow, one such preparation is referred to as "$C_{11-15}$ secondary alcohol 9EO". This product has a total of about 11 to about 15 carbon atoms in the alkyl chain and an average of about 9 moles ethylene oxide per mole of alcohol (n=9). $C_{11-15}$ secondary alcohol ethoxylates such as this are commercially available from Union Carbide Corporation as the Tergitol 15-S series.

Another surfactant which has been found useful according to the present invention is a $C_{12}$ secondary alcohol ethoxylate. Surfactants of this type are commercially available from Union Carbide Corporation as the Tergitol TMN series. An example is referred to herein as "$C_{12}$ branched secondary alcohol 10EO". This product comprises 2,6,8-trimethyl-4-nonanol with an average of about 10 moles ethylene oxide per mole of alcohol (n=10).

To provide the desired rainfastness enhancement of a foliar applied pesticidal or plant growth modifying agent, secondary or tertiary alcohol alkoxylates of the invention may be used at concentrations in the spray solution in the range from about 0.05 to about 2 per cent by volume, preferably from about 0.1 to about 1 per cent by volume, although in certain circumstances greater or lesser concentrations may be used.

In concentrate or ready-to-use glyphosate formulations, the secondary or tertiary alcohol alkoxylate surfactant may usefully be included at weight/weight ratios of said surfactant to glyphosate a.e. from about 1:20 to about 1:1, preferably from about 1:12 to about 1:2 and most preferably from about 1:6 to about 1:3.

In ready-to-use formulations, glyphosate is typically present at about 0.5 to about 2 per cent a.e. by weight. Aqueous concentrate formulations of the invention may contain about 5 to about 40 per cent glyphosate a.e. by weight.

Dry concentrate formulations of the invention may contain about 10 to about 75 per cent glyphosate a.e. by weight. Preferred dry concentrate formulations are water-soluble granules containing about 40 to about 70 per cent glyphosate a.e. by weight.

Preferred glyphosate salts for use in aqueous or dry formulations of the invention include ammonium, alkylamine, for example isopropylamine, alkylsulfonium, for example trimethylsulfonium, and alkali metal salts. Most commonly these salts have a molar ratio of cations to glyphosate anions in the range from about 1:1 to about 2:1.

Long-term shelf stability is an important commercial attribute of concentrate formulations of pesticidal and plant growth modifying agents. In the case of aqueous concentrate formulations, such as those of glyphosate, it is particularly important that surfactants in the formulation do not separate from the other ingredients as a distinct phase. Many such aqueous concentrates show a tendency for phase separation at high temperatures. The minimum temperature at which such phase separation occurs is known as the "cloud point" of the formulation. It is well known to those of skill in the art that most nonionic surfactants, ethoxylated alcohols being a good example, have rather poor compatibility with high ionic strength solutions such as aqueous concentrate formulations of glyphosate salts. This poor compatibility is manifested as a low cloud point, leading to unacceptably poor shelf stability of the formulation.

In accordance with the present invention secondary and tertiary alcohol alkoxylates are incorporated at useful levels in an aqueous concentrate formulation of glyphosate salt by further including in the formulation a compatibilizing agent which raises the cloud point of the formulation to an acceptable level, for example 50° C. or higher.

In both aqueous and dry concentrate glyphosate formulations where rainfastness enhancement is desired, additional surfactant(s) should be included in an amount sufficient to provide acceptable herbicidal efficacy in the absence of rain, and to allow the secondary or tertiary alcohol alkoxylate to exhibit the desired level of rainfastness enhancement.

The amount of such additional surfactant other than secondary or tertiary alcohol alkoxylate to be included depends greatly on the chemical composition of that surfactant, on the plant species targeted and on environmental factors. Normally, however, the weight/weight ratio of secondary or tertiary alcohol alkoxylate to the total of other surfactants is in the range from about 1:20 to about 5:1, preferably from about 1:10 to about 2:1 and most preferably from about 1:5 to about 1:1.

The surfactant(s) additional to secondary or tertiary alcohol alkoxylates in glyphosate compositions of the invention may be selected from alkyl monoglycosides, alkyl polyglycosides, sucrose alkylesters, tertiary or quaternary alkylamine alkoxylates, non-alkoxylated tertiary or quaternary alkylamines, alkylamine oxides, alkylbetaines and the like. Good results have been obtained, for example, with cocoamine 2EO and 5EO (e.g. Ethomeen C/12 and C/15, Akzo Chemicals Inc.), N-methyltallowammonium chloride 5EO, 10EO and 15EO, N-methyloctadecylammonium chloride 15EO (e.g. Ethoquad 18/25, Akzo Chemicals Inc.), N-methylammonium chloride 2EO (formulated at 35% concentration in water as Ethoquad C/12W, Akzo Chemicals Inc.), N-methylcocoammonium chloride 15EO (e.g. Ethoquad C/25, Akzo Chemicals Inc.), N,N-diethyl-N-methylammonium chloride 1EO+7PO (Emcol CC-9, Witco Corporation), N,N-dimethyldodecylamine (Armeen DM12D, Akzo Chemicals Inc.), N,N,N-trimethylcocoammonium chloride (formulated at 33% concentration in water as Arquad C-33W, Akzo Chemicals Inc.), N,N,N-trimethyltallowammonium chloride (formulated at 27% concentration in water as Arquad T-27W, Akzo Chemicals Inc.), potassium laurylbetaine, alkyl polyglucosides (Agrimul PG 2067 and Agrimul PG 2069, Henkel Corporation), $C_{8-10}$ alkyl monoglucoside, and sucrose cocoate (Crodesta SL-40, Croda Inc.).

Several of the Examples herein utilize N-methylcocoammonium chloride with 2 moles ethylene oxide ("cocoamine quat 2EO") as the additional surfactant. Other Examples herein utilize tertiary cocoamine or tallowamine with 5 moles ethylene oxide ("cocoamine 5EO" or "tallowamine 5EO" respectively) as the additional surfactant.

In addition to glyphosate or its salts, the secondary or tertiary alcohol alkoxylate and the additional surfactant(s), any of a variety of further ingredients or adjuvants may be included in formulations of the present invention as long as such added materials are not significantly antagonistic to the glyphosate herbicidal activity and/or to the secondary or tertiary alcohol alkoxylate rainfastness-enhancing activity. Mixtures of glyphosate with other herbicides are also within the scope of the present invention. Examples of such other herbicides include bialaphos, glufosinate, 2,4-D, MCPA, dicamba, diphenylethers, imidazolinones and sulfonylureas.

Methods of use of some glyphosate formulations are well known to those of skill in the art. Aqueous concentrate formulations of the invention are diluted in an appropriate volume of water and applied, for example by spraying, to the weeds or other unwanted vegetation to be killed or controlled. Dry concentrate formulations of the invention are dissolved or dispersed in an appropriate volume of water and applied in the same way.

The present invention is illustrated by but not limited to the following Examples. In describing concentrate compositions of the Examples, percentages are given by weight unless otherwise indicated. In describing concentrations of surfactants in spray solutions, percentages are given by volume.

EXAMPLES

Comparative herbicidal activity with and without simulated rain was determined in greenhouse and field tests. For greenhouse tests, seeds or propagules of selected species were planted in 10.2 cm square pots of soil with added fertilizer. Temperature and relative humidity were allowed to fluctuate within limits defined for each test described in the following Examples. Plants were allowed to grow until the desired growth stage or size (defined for each test) for spraying. Pots were selected for uniformity before treatment and three replicate pots were assigned to each treatment. Spray solutions were prepared by dilution or dissolution of concentrate herbicide formulations in water. When desired to test "tank mix" application of surfactant compositions, these were added to the spray solution at the required concentration. Spraying was performed with a device which simulates agricultural field spraying equipment, delivering a fine spray at a pressure of about 207 kilopascals. Speed of travel of the spray device over the plants was adjusted to give the desired spray volume (defined for each test). For logistical reasons, all three replicates of each treatment were sprayed together. "Rain" treatments were applied by repeated passage of a coarse spray of water over the plants at some desired period of time after herbicide spraying. The amount and duration of "rain" were noted. After spraying and "rain" treatment, the plants were returned to the greenhouse. Herbicidal efficacy was evaluated by visual assessment at one or more selected time periods after treatment and recorded as "percent control" on an arbitrary scale by comparison with untreated plants. On this scale 0 means no visible effect and 100 means death of all plants. In the Examples, percent control values given are the means of three replicates.

In field tests, treatments were applied post-emergence to plants which had grown naturally or from seeds planted mechanically in rows. A randomized block design with three replicates was used, with plot size depending on local circumstances. A backpack sprayer with multiple nozzles giving an overlapping spray pattern was used to maximize uniformity of application. "Rain" was simulated by means of overhead irrigation equipment tested for uniformity of deposition of water. Percent control was evaluated in similar fashion to that described above for greenhouse tests.

Example 1

The following surfactant adjuvants were tested for rainfastness enhancement of glyphosate in a field trial:

Prior Art
   1. Triton AG-98
   2. 2,4,7,9-tetramethyl-5-decyne-4,7-diol 10EO

Invention
   3. $C_{11-15}$ secondary alcohol 9EO
   4. Adjuvant 3+cocoamine quat 2EO (1:1ratio)

In this and other Examples, a number followed by "EO" refers to the average moles of ethylene oxide per mole of surfactant.

Glyphosate was applied as the isopropylamine salt, either without surfactant (the glyphosate formulation sold as Accord® herbicide by Monsanto Company) or with a surfactant based on tallowamine ethoxylate (the glyphosate formulation sold as Roundup® herbicide by Monsanto Company). Triton AG-98 (Union Carbide Corporation) is a widely used low foam commercial agricultural adjuvant, 80% of which is octylphenol ethoxylate.

A total of 11 grass and broadleaf species were planted in rows:

A. *Panicum dichotomiflorum* (fall panicum, PANDI)
   B. *Lolium* sp. (annual ryegrass, LOLSS)
   C. *Bromus tectorum* (downy brome, BROTE)
   D. *Sorghum vulgare.* (grain sorghum cv. Rox Orange, SORGR)
   E. *Echinochloa crus-galli* var. *frumentae* (Japanese millet, ECHCF)
   F. *Echinochloa crus-galli* (barnyardgrass, ECHCG)
   G. *Setaria faberi* (giant foxtail, SETFA)
   H. *Abutilon theophrasti* (velvetleaf, ABUTH)
   I. *Chenopodium album* (common lambsquarters, CHEAL)
   J. *Kochia scoparia* (kochia, KCHSC)
   K. *Salsola kali* (Russian thistle, SASKR)

All applications were made at a spray volume of 10 gallons/acre (93.5 l/ha). To minimize variation in rain-free period, all plots were sprayed within 15 minutes. Rain was simulated by overhead irrigation using an array of fixed sprinklers, which were turned on 60 minutes after the midpoint of the 15-minute glyphosate application period. The sprinklers were left on for 60 minutes, targeting a "rainfall" of at least 0.5 inch (12 mm). Gauges located throughout the experimental area showed that the actual amount of "rain" delivered varied from 11 to 18 mm, with a mean of 14.5 mm.

Data in Table 1 show percent inhibition as recorded 15 days after treatment (DAT) with glyphosate at the rate of 0.25 lb a.e./acre (0.28 kg a.e./ha), without and with "rain" as described above. For all "rain" treatments the adjuvants were applied at a concentration of 0.25% in the spray solution. For the "no rain" treatments, adjuvant 4 was applied at 0.25%, but the other adjuvants were applied, through operator error, at 0.125%. This error does not affect any of the conclusions drawn below from this test.

TABLE 1

Percent inhibition 15 DAT without and with simulated rain (means of 3 replicates).
Adjuvants 1–4 and species A–K as defined in text.

| Glyphosate product | Adjuvant | Rain | A | B | C | D | E | F | G | H | I | J | K |
|---|---|---|---|---|---|---|---|---|---|---|---|---|---|
| Roundup ® | none | no | 86 | 96 | 98 | 95 | 67 | 53 | 100 | 88 | 90 | 81 | 62 |
|  |  | yes | 8 | 28 | 20 | 32 | 22 | 12 | 84 | 32 | 10 | 12 | 10 |
| Roundup ® | 1 | no | 87 | 100 | 100 | 88 | 73 | 68 | 100 | 80 | 92 | 80 | 91 |
|  |  | yes | 13 | 37 | 42 | 48 | 28 | 15 | 96 | 33 | 28 | 17 | 18 |
| Roundup ® | 2 | no | 82 | 100 | 100 | 90 | 85 | 72 | 100 | 88 | 94 | 88 | 75 |
|  |  | yes | 20 | 50 | 50 | 58 | 40 | 15 | 98 | 40 | 38 | 30 | 33 |
| Roundup ® | 3 | no | 85 | 89 | 100 | 94 | 83 | 80 | 100 | 79 | 92 | 87 | 87 |
|  |  | yes | 20 | 57 | 75 | 56 | 37 | 25 | 96 | 38 | 42 | 20 | 20 |
| Roundup ® | 4 | no | 96 | 99 | 100 | 99 | 84 | 77 | 100 | 73 | 93 | 90 | 77 |
|  |  | yes | 18 | 48 | 73 | 57 | 35 | 15 | 94 | 42 | 37 | 25 | 28 |
| Accord ® | 4 | yes | 13 | 59 | 58 | 67 | 42 | 22 | 98 | 42 | 37 | 25 | 28 |

The results of this test show Adjuvant 3 of the invention to provide significant rainfastness enhancement of Roundup. While not giving complete rainfastness under the severe conditions of this test, the use of Adjuvant 3 nevertheless gave greater enhancement of rainfastness than Triton AG-98 (Adjuvant 1 of the prior art) and was at least as effective overall as 2,4,7,9-tetramethyl-5-decyne-4,7-diol 10EO (Adjuvant 2 of the prior art) which is a much higher-cost material. Adjuvant 4 of the invention provided a similar degree of rainfastness enhancement to Adjuvant 3 of the invention, and when added to the surfactantless product Accord gave similar performance with "rain" as when added to the surfactant-containing product Roundup.

Example 2

Aqueous concentrate formulations of the isopropylamine salt of glyphosate were prepared at a glyphosate a.e. loading of 31% (equivalent to about 360 g a.e./liter). All contained 3.5% cocoamine quat 2EO. Secondary or tertiary alcohol ethoxylates of the invention were included at a range of levels and cloud point of the formulation was determined. To measure cloud point, a sample of each formulation in a test tube was heated in a water bath until it became cloudy. The test tube was then removed from the water bath and the sample stirred with a thermometer until it became clear. The temperature at which the sample became clear was recorded as the cloud point of the formulation. Results are shown in Table 2.

TABLE 2

Clouds points (°C.) of glyphosate formulations containing 3.5% cocoamine quat 2EO plus various levels of secondary or tertiary alcohol ethoxylates illustrative of this invention

| 2° or 3° alcohol | % 2° or 3° alcohol in formulation | | | | | | | |
|---|---|---|---|---|---|---|---|---|
|  | 1 | 2 | 3 | 4 | 5 | 6 | 7 | 8 |
| 2°, $C_{11-15}$ 3EO | >95 | <25 | <25 | <25 |  |  |  |  |
| 2°, $C_{11-15}$ 5EO | >95 | >95 | >95 | >95 | <25 |  |  |  |
| 2°, $C_{11-15}$ 7EO | >95 | >95 | >95 | >95 | >95 | <25 | <25 |  |
| 2°, $C_{11-15}$ 9EO | >95 | >95 | >95 | >95 | 89 | 81 | 32 | <25 |
| 2°, $C_{11-15}$ 12EO | >95 | >95 | 88 | 77 | 67 | 56 |  |  |
| 2°, $C_{11-15}$ 15EO |  | 86 | 71 | 57 | 42 | 35 |  |  |
| 3°, $C_{12}$ branched 6EO |  |  |  | >95 | >95 | <25 | <25 |  |
| 3°, $C_{12}$ branched 10EO |  |  |  | >95 | 80 | 72 | 65 |  |

The data for $C_{11-15}$ secondary alcohols show a strong relationship between the EO level on the alcohol and the ability of cocoamine quat 2EO to solubilize the alcohol. Acceptable cloud points (>50° C.) are obtained at up to 6% $C_{11-15}$ secondary alcohol 9EO in the formulation, when cocoamine quat 2EO is present at 3.5%.

Example 3

Aqueous concentrate formulations of the isopropylamine salt of glyphosate were prepared at the same glyphosate a.e. loading as in Example 2, but containing higher levels of cocoamine quat 2EO. Secondary or tertiary alcohol ethoxylates of the invention were included at a range of levels and cloud point of the formulation was determined by the same procedure as in Example 2. Results are shown in Tables 3 and 4.

TABLE 3

Cloud points (° C.) of glyphosate formulations illustrative of this invention containing 5% cocoamine quat 2EO plus various levels of secondary or tertiary alcohol ethoxylates

| 2° or 3° alcohol | % 2° or 3° alcohol | | | |
|---|---|---|---|---|
|  | 5 | 6 | 7 | 8 |
| 2°, $C_{11-15}$ 7EO | >95 | >95 | >95 | >26 |
| 2°, $C_{11-15}$ 9EO | >95 | 87 | 81 | 75 |
| 2°, $C_{11-15}$ 12EO | 76 | 69 | 58 | 48 |
| 3°, $C_{12}$ branched 6EO | >95 | <25 | <25 | <25 |
| 3°, $C_{12}$ branched 10EO | 80 | 68 | 65 | 61 |

TABLE 4

Cloud points (° C.) of glyphosate formulations illustrative of this invention containing 7% cocoamine quat 2EO plus various levels of secondary alcohol ethoxylates

| 2° or 3° alcohol | % 2° or 3° alcohol | | | | | | |
|---|---|---|---|---|---|---|---|
| | 5 | 6 | 7 | 8 | 9 | 10 | 11 |
| 2°, $C_{11-15}$ 7EO | | | | >95 | >95 | <26 | <26 |
| 2°, $C_{11-15}$ 9EO | | | | 85 | 80 | 70 | 65 |
| 2°, $C_{11-15}$ 12EO | 80 | 78 | 66 | 58 | 51 | 42 | 36 |

The data show that acceptable cloud points (>50° C.) are obtained at up to at least 8% $C_{11-15}$ secondary alcohol 9EO in the formulation when cocoamine quat 2EO is present at 5%, and up to at least 11% of this same secondary alcohol in the formulation when cocoamine quat 2EO is present at 7%.

Example 4

Aqueous concentrate formulations of the isopropylamine salt of glyphosate were prepared at a glyphosate a.e. loading of 18.4% (equivalent to about 200 g a.e./liter). All contained 7% cocoamine quat 2EO and 10.2% nonionic surfactant. Formulations of the present invention contained as the nonionic one of several secondary or tertiary alcohol ethoxylates; other formulations were made containing nonionics such as Silwet L-77, 2,4,7,9-tetramethyl-5-decyne-4,7-diol 10EO, nonylphenol 8EO, 10EO and 12EO and $C_{12-15}$ primary alcohol 7EO, 9EO and 12EO. These formulations were tested for rainfastness in a greenhouse test.

The test species was Panicum maximum (guineagrass, PANMA). All glyphosate formulations were applied at 1.5 lb a.e./acre (1.68 kg a.e./ha) in a spray volume of 20 gallons/acre (185 l/ha). Commercial Roundup herbicide was included as a standard. Simulated rain was applied in the amount of 6 mm over a period of 15 minutes, beginning 1 hour after glyphosate treatment. Data on percent inhibition without and with "rain" are presented in Table 5.

TABLE 5

Percent inhibition of guineagrass 15 DAT without and with simulated rain (means of 3 replicates)

| | No rain | Rain |
|---|---|---|
| Roundup ® herbicide (standard) | 100 | 65 |
| Nonionic in formulation: | | |
| Prior Art: | | |
| Silwet L-77 | 100 | 70 |
| 2,4,7,9-tetramethyl-5-decyne-4, 7-diol 10EO | 98 | 94 |
| nonylphenol 8EO | 100 | 97 |
| nonylphenol 10EO | 100 | 81 |
| nonylphenol 12EO | 100 | 63 |
| $C_{12-15}$ primary alcohol 7E0 | 99 | 90 |
| $C_{12-15}$ primary alcohol 9E0 | 98 | 81 |
| $C_{12-15}$ primary alcohol 12E0 | 99 | 68 |
| Invention: | | |
| $C_{11-15}$ secondary alcohol 7E0 | 100 | 89 |
| $C_{11-15}$ secondary alcohol 9E0 | 100 | 99 |
| $C_{11-15}$ secondary alcohol 12E0 | 100 | 86 |

TABLE 5-continued

Percent inhibition of guineagrass 15 DAT without and with simulated rain (means of 3 replicates)

| | No rain | Rain |
|---|---|---|
| $C_{11-15}$ secondary alcohol 15E0 | 99 | 80 |
| $C_{12}$ branched tertiary alcohol 6E0 | 100 | 66 |
| $C_{12}$ branched tertiary alcohol 10EO | 100 | 98 |

In this test, acceptable performance (>85% inhibition) with rain was obtained with 2,4,7,9-tetramethyl-5-decyne-4,7-diol 10EO of the prior art, and with two lower cost materials, nonylphenol 8EO and $C_{12-15}$ primary alcohol 7EO, likewise outside the scope of the present invention. It will be noted that even a slight increase in the EO level on either the nonylphenol or the primary alcohol significantly reduced the rainfastness of the formulation; at the 12EO level no rainfastness advantage at all was obtained with either of these surfactant types. By contrast, $C_{11-15}$ secondary alcohol surfactants of the invention gave enhanced rainfastness over a wide range of EO levels. Of the $C_{12}$ branched tertiary alcohol surfactants tested, the 10EO example gave excellent rainfastness while the 6EO example did not give significant rainfastness enhancement in this test.

Example 5

Aqueous concentrate formulations of the isopropylamine salt of glyphosate were prepared at a glyphosate a.e. loading of 31% (equivalent to about 360 g a.e./liter). All contained 7.5% cocoamine quat 2EO and 8.6% nonionic surfactant. Formulations of the present invention contained as the nonionic $C_{11-15}$ secondary alcohol 9EO or $C_{12}$ branched tertiary alcohol 10EO; for comparison, other formulations were made containing nonionics disclosed as rainfastness aids in the prior art such as 2,4,7,9-tetramethyl-5-decyne-4,7-diol 10EO or nonylphenol 8EO. These formulations were tested for rainfastness in a greenhouse test.

The test species was Elymus repens (quackgrass, AGRRE). All glyphosate formulations were applied at both 0.75 and 1.5 lb a.e./acre (0.84 and 1.68 kg a.e./ha) in a spray volume of 20 gallons/acre (187 l/ha). Commercial Roundup herbicide was included as a standard. Simulated rain was applied in the amount of 6 mm over a period of 15 minutes, beginning 1 hour after glyphosate treatment. Data on percent inhibition without and with "rain" are presented in Table 6.

TABLE 6

Percent inhibition of quackgrass 28 DAT without and with simulated rain (means of 3 replicates)

| | Application rate lb/a (kg/h) | | | |
|---|---|---|---|---|
| | 0.75 (0.84) | | 1.5 (1.68) | |
| | No rain | Rain | No rain | Rain |
| Roundup (standard) | 73 | 30 | 92 | 72 |
| Nonionic in formulation: | | | | |
| 2,4,7,9-tetramethyl-5-decyne-4,7-diol 10EO | 94 | 78 | 98 | 94 |
| nonylphenol 8EO | 97 | 83 | 98 | 79 |
| $C_{11-15}$ secondary alcohol 9EO | 93 | 96 | 100 | 98 |
| $C_{12}$ branched tertiary alcohol 10EO | 94 | 84 | 100 | 88 |

At the lower glyphosate rate, both formulations of the present invention gave better rainfastness than the formulation of the prior art containing 2,4,7,9-tetramethyl-5-decyne-4,7-diol 10EO, and the formulation of the invention containing $C_{11-15}$ secondary alcohol 9EO gave better rainfastness than either of the prior art formulations. At the higher glyphosate rate, both formulations of the present invention gave better rainfastness than the formulation of the prior art containing nonylphenol 8EO, and gave comparable rainfastness to the much higher cost formulation containing 2,4,7,9-tetramethyl-5-decyne-4,7-diol 10EO.

Considering Examples 4 and 5 together, it is clear that $C_{11-15}$ secondary alcohol 9EO and $C_{12}$ branched tertiary alcohol 10EO of the present invention are more consistent in their rainfastness enhancing performance than nonylphenol ethoxylates of the prior art.

Example 6

The following glyphosate formulations were tested for herbicidal activity and rainfastness by comparison with Roundup® herbicide in a field trial:
Formulation A (representative of the prior art): 31% glyphosate a.e. as the isopropylamine salt, 7.5% cocoamine quat 2EO, 8.6% nonylphenol 8EO.
Formulation B (representative of the present invention): 31% glyphosate a.e. as the isopropylamine salt, 7.5% cocoamine quat 2EO, 8.6% $C_{11-15}$ secondary alcohol 9EO.

A total of 7 grass and broadleaf species were planted in rows:

L. *Digitaria ciliaris* (southern crabgrass, DIGSP)
M. *Brachiaria platyphylla* (broadleaf signalgrass, BRAPP)
N. *Sorghum halepense* (johnsongrass, SORHA)
O. *Echinochloa crus-galli* (barnyardgrass, ECHCG)
P. *Sida spinosa* (prickly sida, SIDSP)
Q. *Echinochloa crus-galli* var. *frumentae* (Japanese millet, ECHCF)
R. *Sesbania exaltata* (hemp sesbania, SEBEX)

All applications were made at a spray volume of 10 gallons/acre (93.5 l/ha). To minimize variation in rain-free period, all plots were sprayed within 15 minutes. Rain was simulated by overhead irrigation using a lateral move irrigation system, which was turned on 60 minutes after the midpoint of the 15-minute glyphosate application period to give a "rainfall" of approximately 0.5 inch (12 mm).

Data in Table 7 show percent inhibition as recorded 21 days after treatment (DAT) with glyphosate at the rate of 0.75 lb a.e./acre (0.84 kg a.e./ha), without and with "rain" as described above.

TABLE 7

Percent inhibition 21 DAT without and with simulated rain (means of 3 replicates).
Formulations A and B and species L–R as defined in text.

| Formulation | Rain | L | M | N | O | P | Q | R |
|---|---|---|---|---|---|---|---|---|
| Roundup (standard) | no | 98 | 95 | 99 | 86 | 75 | 90 | 77 |
|  | yes | 65 | 57 | 86 | 52 | 65 | 78 | 68 |
| A (prior art) | no | 100 | 93 | 99 | 87 | 77 | 89 | 69 |
|  | yes | 79 | 70 | 93 | 62 | 68 | 82 | 75 |
| B (invention) | no | 100 | 92 | 95 | 79 | 73 | 89 | 72 |
|  | yes | 87 | 75 | 96 | 68 | 77 | 84 | 82 |

Examples 7–14

In the field tests of Examples 7–14 all applications were made at a spray volume of 93.5 l/ha. Although the compositions tested contained different concentrations of glyphosate a.e., all were tested at equal product rate, measured in l/ha. Thus compositions having a lower glyphosate a.e. loading than the standard (Roundup® herbicide) were tested at reduced glyphosate a.e. rate versus the standard.

Formulation C shown in Examples 7–14 and Formulations D–G shown in Example 13 have the following compositions:

| Formulation C | |
|---|---|
| glyphosate as sesquiammonium salt | 270 g a.e./l |
| tallowamine 5EO | 10.9% w/w |
| $C_{11-15}$ secondary alcohol 9EO | 5.2% w/w |
| water | to 100% w/w |
| Formulation D | |
| glyphosate as isopropylamine salt | 300 g a.e./l |
| cocoamine 5EO | 10.9% w/w |
| $C_{11-15}$ secondary alcohol 9EO | 6.8% w/w |
| water | to 100% w/w |
| Formulation E | |
| glyphosate as isopropylamine salt | 270 g a.e./l |
| cocoamine 5EO | 9.8% w/w |
| $C_{11-15}$ secondary alcohol 9EO | 6.2% w/w |
| water | to 100% w/w |
| Formulation F | |
| glyphosate as isopropylamine salt | 240 g a.e./l |
| cocoamine 5EO | 9.8% w/w |
| $C_{11-15}$ secondary alcohol 9EO | 6.2% w/w |
| water | to 100% w/w |
| Formulation G | |
| glyphosate as isopropylamine salt | 240 g a.e./l |
| tallowamine 5EO | 9.8% w/w |
| $C_{11-15}$ secondary alcohol 9EO | 6.2% w/w |
| water | to 100% w/w |

Examples 7–14 represent field tests conducted on Monsanto's experimental farms in the USA in which at least Formulation C of the invention was compared with Roundup herbicide. A total of 129 head-to-head comparisons of Roundup and Formulation C (different product rates on different species in different tests) are shown in Examples 7–14. The grand means for all 129 comparisons are 78.5% control by Roundup and 78.6% control by Formulation C. These means are almost exactly equal. In 76 of the 129 comparisons the percent control by Formulation C was equal to or within 5 percentage points of that by Roundup. In 27 of the 129 comparisons, Formulation C gave poorer control than Roundup by a margin greater than 5 percentage points. In 26 of the 129 comparisons, Formulation C gave better control than Roundup by a margin greater than 5 percentage points. It will be readily appreciated by those of skill in the art that the normal variability of field performance is sufficient to explain the variation in relative performance and that the results set out in Examples 7–14 are indicative of Formulation C being substantially equal in herbicidal efficacy to Roundup at equal product rate, in spite of the 25% lower glyphosate a.e. rate delivered by Formulation C.

Example 7

This test was conducted on an experimental farm at Monmouth, Ill. Artificially established stands of kochia (*Kochia scoparia*, KCHSC), wild buckwheat (*Polygonum convolvulus*, POLCO), wild mustard (*Sinapis arvensis*, SINAR), Indian mustard (*Brassica juncea*, BRSJU), perennial ryegrass (*Lolium perenne*, LOLPE), downy brome (*Bromus tectorum*, BROTE), wild oat (*Avena fatua*, AVEFA)

and spring wheat (*Triticum aestivum*, TRZAS) were treated by spraying in late spring. Herbicidal efficacy was evaluated 25 days after treatment.

| Formulation | | | % CONTROL | | | |
|---|---|---|---|---|---|---|
| Weed Species: | ml/ha | kg/a.e./ha | KCHSC | POLCO | SINAR | BRSJU |
| RU | 388 | 0.14 | 13 | 13 | 17 | 7 |
| RU | 789 | 0.28 | 58 | 22 | 28 | 27 |
| RU | 1571 | 0.56 | 76 | 37 | 76 | 65 |
| Formulation C | 388 | 0.11 | 20 | 13 | 15 | 8 |
| Formulation C | 789 | 0.21 | 52 | 15 | 53 | 38 |
| Formulation C | 1571 | 0.42 | 79 | 33 | 79 | 63 |

| Formulation | | | % CONTROL | | | |
|---|---|---|---|---|---|---|
| Weed Species: | ml/ha | kg/a.e./ha | LOLPE | BROTE | AVEFA | TRZAS |
| RU | 388 | 0.14 | 27 | 23 | 27 | 27 |
| RU | 789 | 0.28 | 50 | 71 | 68 | 75 |
| RU | 1571 | 0.56 | 78 | 92 | 93 | 93 |
| Formulation C | 388 | 0.11 | 28 | 38 | 45 | 35 |
| Formulation C | 789 | 0.21 | 62 | 89 | 79 | 83 |
| Formulation C | 1571 | 0.42 | 86 | 100 | 99 | 97 |

Example 8

This test was conducted on an experimental farm at Loxley, Ala. Artificially established stands of Japanese millet (*Echinochloa crus-galli*, ECHCF), johnsongrass (*Sorghum halepense*, SORHA), barnyardgrass (*Echinochloa crus-galli*, ECHCG), smooth pigweed (*Amaranthus hybridus*, AMACH), prickly sida (*Sida spinosa*, SIDSP), hemp sesbania (*Sesbania exaltata*, SEBEX), sicklepod (*Cassia obtusifolia*, CASOB) and morningglory (Ipomoea spp., IPOSS) were treated by spraying in late spring. Herbicidal efficacy was evaluated 25 days after treatment.

| Formulation | | kg/ | % CONTROL | | | |
|---|---|---|---|---|---|---|
| Weed Species: | ml/ha | a.e./ha | ECHCF | SORHA | ECHCG | AMACH |
| RU | 1770 | 0.63 | 100 | 100 | 98 | 92 |
| RU | 2360 | 0.84 | 100 | 100 | 98 | 97 |
| RU | 3540 | 1.25 | 100 | 100 | 100 | 100 |
| Formulation C | 1770 | 0.47 | 100 | 100 | 100 | 87 |
| Formulation C | 2360 | 0.63 | 100 | 100 | 100 | 91 |
| Formulation C | 3540 | 0.94 | 100 | 100 | 100 | 100 |

| Formulation | | lb a.e./ | % CONTROL | | | |
|---|---|---|---|---|---|---|
| Weed Species: | ml/ha | acre | SIDSP | SEBEX | CASOB | IPOSS |
| RU | 1770 | 0.63 | 87 | 68 | 81 | 60 |
| RU | 2360 | 0.84 | 98 | 65 | 93 | 67 |
| RU | 3540 | 1.25 | 98 | 88 | 97 | 80 |
| Formulation C | 1770 | 0.47 | 76 | 60 | 80 | 57 |
| Formulation C | 2360 | 0.63 | 88 | 80 | 92 | 67 |
| Formulation C | 3540 | 0.94 | 95 | 83 | 100 | 75 |

Example 9

This test was conducted on an experimental farm at Jerseyville, Ill. Artificially established stands of morningglory (Ipomoea spp., IPOSS), hemp sesbania (*Sesbania exaltata*, SEBEX), prickly sida (Sida spinosa, SIDSP) and Japanese millet (*Echinochloa crus-galli*, ECHCF) were treated by spraying in late spring. Herbicidal efficacy was evaluated 22 days after treatment.

| Formulation | | | % CONTROL | | | |
|---|---|---|---|---|---|---|
| Weed Species: | ml/ha | kg a.e./ha | IPOSS | SEBEX | SIDSP | ECHCF |
| RU | 1180 | 0.42 | 38 | 85 | 94 | 92 |
| RU | 1770 | 0.63 | 55 | 94 | 98 | 100 |
| RU | 2360 | 0.84 | 70 | 98 | 99 | 100 |
| Formulation C | 1180 | 0.31 | 32 | 88 | 86 | 86 |
| Formulation C | 1770 | 0.47 | 44 | 90 | 92 | 94 |
| Formulation C | 2360 | 0.62 | 58 | 95 | 98 | 100 |

Example 10

This test was conducted on an experimental farm at Jerseyville, Ill. Artificially established stands of wheat (*Triticum aestivum*, TRZAW) and giant foxtail (*Setaria faberi*, SETFA) were treated by spraying in late spring. Herbicidal efficacy was evaluated 28 days after treatment.

| Formulation | | | % control | |
|---|---|---|---|---|
| Weed Species: | ml/ha | kg a.e./ha | TRZAW | SETFA |
| RU | 388 | 0.14 | 57 | 77 |
| RU | 789 | 0.28 | 99 | 96 |
| RU | 1180 | 0.42 | 100 | 100 |
| Formulation C | 388 | 0.11 | 65 | 68 |
| Formulation C | 789 | 0.21 | 94 | 91 |
| Formulation C | 1180 | 0.31 | 100 | 100 |

Example 11

This test was conducted on an experimental farm at Jerseyville, Ill. Artificially established stands of giant foxtail (*Setaria faberi*, SETFA) and common ragweed (*Ambrosia artemisiifolia*, AMBEL) were treated by spraying in late spring. Herbicidal efficacy was evaluated 24 days after treatment.

| Formulation | | | % CONTROL | |
|---|---|---|---|---|
| Weed Species: | ml/ha | kg a.e./ha | SETFA | AMBEL |
| RU | 388 | 0.14 | 93 | 59 |
| RU | 789 | 0.28 | 100 | 100 |
| RU | 1180 | 0.42 | 100 | 100 |
| Formulation C | 388 | 0.11 | 85 | 53 |
| Formulation C | 789 | 0.22 | 97 | 94 |
| Formulation C | 1180 | 0.31 | 100 | 100 |

Example 12

This test was conducted on an experimental farm at Monmouth, Ill. Artificially established stands of velvetleaf (*Abutilon theophrasti*, ABUTH), giant ragweed (*Ambrosia trifida*, AMBTR), redroot pigweed (*Amaranthus retroflexus*, AMARE), common lambsquarters (*Chenopodium album*, CHEAL), Japanese millet (*Echinochloa crus-galli*, ECHCF), barnyardgrass (*Echinochloa crus-galli*, ECHCG) and giant foxtail (*Setaria faberi*, SETFA) were treated by spraying in late spring. Herbicidal efficacy was evaluated 28 days after treatment.

| Formulation Weed Species: | ml/ha | kg a.e./ ha | % CONTROL | | | |
|---|---|---|---|---|---|---|
| | | | ABUTH | AMBTR | AMARE | CHEAL |
| RU | 789 | 0.28 | 23 | 23 | 58 | 58 |
| RU | 1180 | 0.42 | 52 | 63 | 81 | 71 |
| RU | 1571 | 0.56 | 67 | 70 | 87 | 95 |
| Formulation C | 789 | 0.22 | 38 | 40 | 82 | 77 |
| Formulation C | 1180 | 0.31 | 43 | 72 | 86 | 83 |
| Formulation C | 1571 | 0.42 | 42 | 60 | 73 | 82 |

| Formulation Weed Species | ml/ha | kg a.e./ha | % CONTROL | | |
|---|---|---|---|---|---|
| | | | ECHCF | ECHCG | SETFA |
| RU | 789 | 0.28 | 82 | 79 | 93 |
| RU | 1180 | 0.42 | 89 | 84 | 98 |
| RU | 1571 | 0.56 | 100 | 88 | 98 |
| Formulation C | 789 | 0.22 | 94 | 99 | 97 |
| Formulation C | 1180 | 0.31 | 91 | 94 | 97 |
| Formulation C | 1571 | 0.42 | 95 | 88 | 99 |

Example 13

This test was conducted on an experimental farm at Jerseyville, Ill. Artificially established stands of hemp sesbania (*Sesbania exaltata*, SEBEX), giant foxtail (*Setaria faberi*, SETFA), Japanese millet (*Echinochloa crus-galli*, ECHCF), velvetleaf (*Abutilon theophrasti*, ABUTH) and morningglory (Ipomoea spp., IPOSS) were treated by spraying in early summer. Herbicidal efficacy was evaluated 23 days after treatment.

| Formulation | ml/ha | kg a.e./ha | % CONTROL | | | | |
|---|---|---|---|---|---|---|---|
| | | | SEBEX | SETFA | ECHCF | ABUTH | IPOSS |
| RU | 1180 | 0.42 | 67 | 100 | 98 | 64 | 64 |
| RU | 1571 | 0.56 | 80 | 100 | 97 | 75 | 75 |
| RU | 2360 | 0.84 | 85 | 100 | 100 | 85 | 77 |
| Formulation C | 1180 | 0.31 | 63 | 100 | 100 | 58 | 52 |
| Formulation C | 1571 | 0.42 | 85 | 100 | 99 | 71 | 67 |
| Formulation C | 2360 | 0.62 | 85 | 100 | 98 | 81 | 75 |
| Formulation D | 1180 | 0.35 | 73 | 100 | 99 | 63 | 58 |
| Formulation D | 1571 | 0.47 | 72 | 100 | 100 | 75 | 67 |
| Formulation D | 2360 | 0.70 | 88 | 100 | 100 | 76 | 72 |
| Formulation E | 1180 | 0.31 | 60 | 100 | 90 | 61 | 43 |
| Formulation E | 1571 | 0.42 | 69 | 100 | 100 | 63 | 65 |
| Formulation E | 2360 | 0.62 | 89 | 100 | 100 | 81 | 66 |
| Formulation F | 1180 | 0.28 | 57 | 100 | 99 | 53 | 52 |
| Formulation F | 1571 | 0.37 | 76 | 100 | 95 | 65 | 52 |
| Formulation F | 2360 | 0.56 | 82 | 100 | 98 | 77 | 70 |
| Formulation G | 1180 | 0.28 | 63 | 100 | 96 | 63 | 50 |
| Formulation G | 1571 | 0.37 | 65 | 100 | 100 | 71 | 63 |
| Formulation G | 2360 | 0.56 | 81 | 100 | 100 | 78 | 65 |

Example 14

This test was conducted on an experimental farm at Jerseyville, Ill. Artificially established stands of Japanese millet (*Echinochloa crus-galli*, ECHCF), broadleaf signalgrass (*Brachiaria platyphylla*, BRAPP), prickly sida (*Sida spinosa*, SIDSP), redroot pigweed (*Amaranthus retroflexus*, AMARE), hemp sesbania (*Sesbania exaltata*, SEBEX), morningglory (Ipomoea spp., IPOSS) and velvetleaf (*Abutilon theophrasti*, ABUTH) were treated by spraying in late summer. Herbicidal efficacy was evaluated 32 days after treatment.

| Formulation Weed Species: | ml/ha | kg a.e./ha | % CONTROL | | | |
|---|---|---|---|---|---|---|
| | | | ECHCF | BRAPP | SIDSP | AMARE |
| RU | 885 | 0.31 | 97 | 98 | 81 | 95 |
| RU | 1770 | 0.62 | 100 | 100 | 95 | 99 |
| RU | 2360 | 0.84 | 100 | 100 | 99 | 99 |
| Formulation C | 885 | 0.24 | 99 | 100 | 46 | 95 |
| Formulation C | 1770 | 0.47 | 100 | 100 | 89 | 98 |
| Formulation C | 2360 | 0.62 | 100 | 100 | 97 | 100 |

| Formulation Weed Species | ml/ha | kg a.e./ha | % CONTROL | | |
|---|---|---|---|---|---|
| | | | SEBEX | IPOSS | ABUTH |
| RU | 885 | 0.24 | 98 | 52 | 52 |
| RU | 1770 | 0.62 | 99 | 68 | 66 |
| RU | 2360 | 0.84 | 100 | 87 | 81 |
| Formulation C | 885 | 0.24 | 100 | 47 | 42 |
| Formulation C | 1770 | 0.47 | 100 | 69 | 69 |
| Formulation C | 2360 | 0.62 | 100 | 86 | 88 |

Examples 15–16

In Examples 15 and 16, a short-term whole plant assay was used to evaluate relative efficacy of aqueous glyphosate compositions containing tallowamine 5EO and $C_{11-15}$ secondary alcohol 9EO in different concentrations and proportions relative to one another.

Equal volumes of uniformly sized seeds (20–25 in number) of barley cv. Pennco were sown in a growing medium consisting of a 3:2:1 sand/soil/peat mixture in 4 inch square plastic pots. Pots were placed in a controlled environment growth chamber providing a 14 hour photoperiod, day and night temperatures of 78° F. and 66° F. respectively, and a relative humidity in the range from 30% to 50%. Light was provided by a combination of metal halide and sodium vapor lamps. All pots were bottom watered at 1200 hr on the first day, resulting in rapid saturation of the growing medium. Seedling emergence occurred on the third and fourth days. On the seventh day, all pots were fertilized by bottom watering with a Peters 20-20-20 fertilizer containing 475 ppm soluble nitrogen.

On the eighth day, pots were sorted into 6 replicate blocks according to plant size. Treatments, including no-treatment controls, were randomly assigned within each block, one treatment per pot.

Plants were treated with glyphosate compositions in rapid succession between 0830 hr and 0900 hr on the ninth day, when average plant height was 13–15 cm and the second leaf was just beginning to elongate. Compositions were applied using a calibrated single-nozzle track sprayer delivering 187 l/ha through a Teejet 8001E nozzle at 276 kilopascals. Plants were removed from the growth chamber immediately before treatment and returned to the same growth chamber immediately after treatment. Pots were spatially arranged in a randomized complete block experimental design. At 6 hours after treatment plants in all pots were trimmed by cutting to 20 mm above the top edge of the pot. This removed approximately 90% of the barley leaf area. Pots were bottom watered once daily for the remainder of the study. Data collection took place on the sixteenth day, 7 days after treatment.

Average height of barley regrowth in each pot was measured to the nearest 5 mm increment, from the earlier cutting height 20 mm above the edge of the pot. All plants in each pot were then cut at 20 mm above the edge of the pot and total fresh weight was recorded.

Example 15

All compositions in this Example contained glyphosate as the isopropylamine salt at a concentration calculated to deliver 0.42 kg a.e./ha. Polyoxyethylene tallowamine 5EO (T/Am 5) concentration was varied independently of $C_{11-15}$ secondary alcohol 9EO (S/Al 9) concentration as will be clear from the tables below. Untreated plants had a mean regrowth height of 175 mm.

| T/Am 5 | S/Al 9 (% w/v) | | | | | |
|---|---|---|---|---|---|---|
| (% w/v) | 0 | 0.15 | 0.3 | 0.45 | 0.6 | 0.75 |
| Mean height of regrowth (mm) | | | | | | |
| 0 | 148 | 101 | 112 | 124 | 120 | 122 |
| 0.05 | 149 | 52 | 39 | 51 | 55 | 66 |
| 0.1 | 64 | 51 | 49 | 51 | 60 | 63 |
| 0.15 | 65 | 53 | 50 | 47 | 46 | 52 |
| 0.2 | 58 | 50 | 45 | 52 | 54 | 52 |
| 0.25 | 57 | 47 | 45 | 43 | 47 | 42 |
| Least significant difference (P = 0.05) 15 | | | | | | |
| Mean fresh weight of regrowth (g) | | | | | | |
| 0 | 1.92 | 1.24 | 1.34 | 1.46 | 1.43 | 1.45 |
| 0.05 | 1.80 | 0.70 | 0.54 | 0.61 | 0.77 | 0.90 |
| 0.1 | 0.83 | 0.75 | 0.68 | 0.69 | 0.80 | 0.80 |
| 0.15 | 0.78 | 0.68 | 0.72 | 0.65 | 0.61 | 0.67 |
| 0.2 | 0.73 | 0.61 | 0.62 | 0.71 | 0.68 | 0.66 |
| 0.25 | 0.76 | 0.56 | 0.56 | 0.59 | 0.68 | 0.61 |
| Least significant difference (P = 0.05) 0.20 | | | | | | |

In this study, when S/Al 9 was the sole surfactant, the lowest tested concentration (0.15%) was the most effective in potentiating glyphosate activity, there being a slight tendency for performance to deteriorate as concentration was increased above this level. When T/Am 5 was the sole surfactant, the lowest tested concentration (0.05%) gave little or no improvement in glyphosate efficacy, but a concentration of 0.1% gave very significant improvement. No further improvement was seen as T/Am 5 concentration was increased above 0.1%.

When T/Am 5 concentration was 0.1% or higher, adding S/Al 9 gave little further improvement in glyphosate efficacy in this study. However, at 0.05% T/Am 5, addition of S/Al 9 gave a response far in excess of any response that could have been predicted from the weak performance of S/Al 9 alone. This study therefore clearly shows a synergistic interaction between S/Al 9 and T/Am 5 at suboptimal levels of T/Am 5.

Example 16

A further study was conducted to focus greater attention on low T/Am 5 concentrations and to try to confirm a synergistic interaction between T/Am 5 and S/Al 9 at such low T/Am 5 concentrations. Glyphosate rates in this study were also lower (0.07, 0.14 and 0.28 kg a.e./ha). All compositions in this Example contained glyphosate as the monoisopropylamine salt. T/Am 5 concentration was again varied independently of S/Al 9 concentration as will be clear from the tables below, in which results for all three glyphosate rates are averaged. Untreated plants had a mean regrowth height of 168 mm.

| T/Am 5 | S/Al 9 (% w/v) | | | | | |
|---|---|---|---|---|---|---|
| (% w/v) | 0 | 0.031 | 0.062 | 0.125 | 0.25 | 0.5 |
| Mean height of regrowth (mm) | | | | | | |
| 0 | 171 | 144 | 145 | 151 | 156 | 165 |
| 0.016 | 124 | 87 | 88 | 91 | 93 | 120 |
| 0.031 | 118 | 90 | 84 | 85 | 93 | 99 |
| 0.062 | 123 | 92 | 79 | 79 | 79 | 98 |
| 0.125 | 116 | 92 | 88 | 86 | 84 | 85 |
| 0.25 | 113 | 84 | 85 | 75 | 73 | 78 |
| Least significant difference (P = 0.05) 11 | | | | | | |
| Mean fresh weight of regrowth (g) | | | | | | |
| 0 | 2.83 | 2.16 | 2.28 | 2.31 | 2.44 | 2.98 |
| 0.016 | 1.82 | 1.32 | 1.24 | 1.33 | 1.40 | 1.90 |
| 0.031 | 1.64 | 1.46 | 1.33 | 1.25 | 1.32 | 1.51 |
| 0.062 | 1.75 | 1.44 | 1.18 | 1.28 | 1.18 | 1.47 |
| 0.125 | 1.72 | 1.39 | 1.36 | 1.34 | 1.37 | 1.32 |
| 0.25 | 1.71 | 1.32 | 1.32 | 1.19 | 1.21 | 1.28 |
| Least significant difference (P = 0.05) 0.20 | | | | | | |

As in the previous study (Example 15), when S/Al 9 was the sole surfactant, the lowest tested concentration, in this case just 0.031%, was the most effective in potentiating glyphosate activity, there being once again a slight tendency for performance to deteriorate as concentration was increased above this level. When T/Am 5 was the sole surfactant, all concentrations, even as low as 0.016%, gave significant improvement in glyphosate efficacy. No significant further improvement was seen as T/Am 5 concentration was increased above 0.016%.

Adding S/Al 9 to T/Am 5 improved glyphosate efficacy beyond that achievable with T/Am 5 alone. In this study, the improvement was seen with all combinations except for combinations of high S/Al 9 and low T/Am 5 concentration. In most cases addition to T/Am 5 of S/Al 9 gave a response far in excess of any response that could have been predicted from the weak performance of S/Al 9 alone. This study therefore confirms the synergistic interaction between S/Al 9 and T/Am 5.

Comparisons may be drawn between certain 1:1 combinations of S/Al 9 and T/Am 5 and either S/Al 9 alone or T/Am alone at the same total surfactant concentration as shown in the following table.

| Mean fresh weight of regrowth (g) | | | |
|---|---|---|---|
| Total surfactant concentration | T/Am 5 alone | 1:1 combination | S/Al 9 alone |
| 0.062 | 1.75 | 1.46 | 2.28 |
| 0.125 | 1.72 | 1.18 | 2.31 |
| 0.25 | 1.71 | 1.34 | 2.44 |

In all cases the fresh weight reduction is greater with the combination of surfactants than with either surfactant alone at the same total concentration.

While the illustrative embodiments of the invention have been described with particularity, it will be understood that various other modifications will be apparent to and can readily be made by one of skill in the art without departing from the spirit and scope of the invention.

What is claimed is:

1. A storage-stable, aqueous non-oily liquid or dry concentrate agriculturally acceptable composition comprising:
   (a) glyphosate or one or more of its salts or mixtures thereof;
   (b) one or more secondary alcohol surfactants having the representative chemical structure

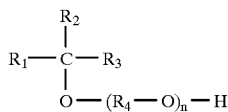

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups and n is an average number from about 3 to about 30, said secondary alcohol imparting rainfastness to the composition; and
   (c) one or more other surfactants selected from the group consisting of alkyl monoglycosides, alkyl polyglycosides, sucrose alkylesters, tertiary and quaternary alkylamine alkoxylates, non-alkoxylated tertiary and quaternary alkylamines, alkylamine oxides and alkylbetaines.

2. The composition of claim 1 wherein, in the structure of said alcohol surfactant, $R_1$ and $R_2$ are both straight chain alkyl groups with a total of about 7 to about 30 carbon atoms, and $R_4$ groups are ethylene.

3. The composition of claim 2 wherein, in the structure of said alcohol surfactant, n is an average number from about 7 to about 14.

4. The composition of claim 2 wherein, in the structure of said alcohol surfactant, n is an average numbers from about 9 to about 12.

5. The composition of claim 1 which is an aqueous concentrate formulation with a glyphosate acid equivalent loading in the range from about 5 to about 40 per cent by weight.

6. The composition of claim 1 which is a dry concentrate composition with a glyphosate acid equivalent loading in the range from about 10 to about 75 per cent by weight.

7. The composition of claim 6 which is a water-soluble granular formulation with a glyphosate acid equivalent loading in the range from about 40 to about 70 per cent by weight.

8. The composition of claim 1 wherein said alcohol surfactant comprises a $C_{11-15}$ unbranched alkyl chain with an ethoxylated alcohol group at any position on the chain except at either end, and n is an average number from about 9 to about 12.

9. The composition of claim 8 comprising said alcohol surfactant and a tertiary alkylamine surfactant with about 2 to about 10 moles of ethylene oxide per mole of amine.

10. The composition of claim 9 wherein said tertiary alkylamine surfactant is a cocoamine or tallowamine with about 2 to about 5 moles of ethylene oxide per mole of amine.

11. The composition of claim 8 comprising said alcohol surfactant and a quaternary alkylamine surfactant with about 2 to about 10 moles of ethylene oxide per mole of amine.

12. The composition of claim 11 wherein said quaternary alkylamine surfactant is a cocoamine or tallowamine with about 2 to about 5 moles of ethylene oxide per mole of amine.

13. The composition of claim 10 or claim 12 wherein the weight ratio of said alcohol surfactant to glyphosate acid equivalent is in the range from about 1:20 to about 1:1.

14. The composition of claim 10 or claim 12 wherein the weight ratio of said alcohol surfactant to glyphosate acid equivalent is in the range from about 1:12 to about 1:2.

15. The composition of claim 10 or claim 12 wherein the weight ratio of said alcohol surfactant to glyphosate acid equivalent is in the range from about 1:6 to about 1:3.

16. The composition of claim 10 or claim 12 wherein the weight ratio of said alcohol surfactant to said tertiary or quaternary alkylamine surfactant is in the range from about 1:20 to about 5:1.

17. The composition of claim 10 or claim 12 wherein the weight ratio of said alcohol surfactant to said tertiary or quaternary alkylamine surfactant is in the range from about 1:10 to about 2:1.

18. The composition of claim 10 or claim 12 wherein the weight ratio of said alcohol surfactant to said tertiary or quaternary alkylamine surfactant is in the range from about 1:5 to about 1:1.

19. A storage-stable aqueous concentrate herbicidal composition comprising:
   (a) at least 240 g/l of glyphosate acid equivalent in the form of the ammonium salt of glyphosate, wherein the molar ratio of ammonium cations to glyphosate anions is in the range from about 1:1 to about 2:1;
   (b) an ethoxylated $C_{11-15}$ secondary alcohol surfactant having an average of about 9 moles of ethylene oxide per mole of secondary alcohol; said ethoxylated $C_{11-15}$ secondary alcohol surfactant imparting rainfastness to the composition and
   (c) an ethoxylated tertiary cocoamine or tallowamine surfactant having an average of about 5 moles of ethylene oxide per mole of amine;

wherein the ratio of glyphosate, expressed as acid equivalent weight, to the total weight of secondary alcohol and cocoamine or tallowamine surfactants is in the range from about 4:1 to about 1.5:1, and the weight/weight ratio of secondary alcohol surfactant to cocoamine or tallowamine surfactant is in the range from about 5:1 to about 1:1.

20. A non-oily aqueous surfactant composition for enhancing the efficacy of a glyphosate herbicide, comprising:
   (a) an ethoxylated secondary alcohol surfactant having the representative chemical structure

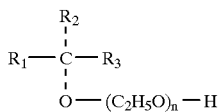

wherein $R_1$ and $R_2$ are independently straight chain alkyl groups, the total number of carbon atoms in $R_1$ and $R_2$ is in the range from about 10 to about 20, and n is an average number in the range from about 7 to about 14; said ethoxylated secondary alcohol surfactant imparting rainfastness to the composition and (b) an ethoxylated alkylamine surfactant having an average alkyl chain length in the range from about 10 to about 20 carbon atoms and having an average of from about 2 to about 20 moles of ethylene oxide per mole of amine, said alkylamine surfactant being selected from the group consisting of tertiary alkylamines, quaternary alkylamines and alkylamine oxides.

21. A method of controlling unwanted vegetation comprising the steps of:

(a) dissolving or diluting in water in a spray tank a mixture of a glyphosate herbicide and a composition of claim 20 to form a spray solution; and (b) applying the spray solution by spraying to the foliage of said vegetation.

22. A herbicidal method comprising adding to a glyphosate composition a secondary alcohol surfactant having the representative chemical structure

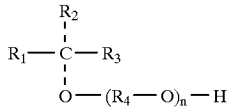

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups and n is an average number from about 3 to about 30, and thereafter applying the composition to unwanted vegetation prior to the onset of rain which would reduce the herbicidal efficacy of an otherwise similar composition lacking only the secondary alcohol surfactant.

23. A method of controlling unwanted vegetation comprising the steps of:

(a) dissolving or diluting in water in a spray tank a composition of claim 10 or claim 19 to form a spray solution; and (b) applying the spray solution by spraying to the foliage of said vegetation;

said method giving acceptable control in the absence of rain where the glyphosate acid equivalent rate applied is at least about 25% lower than the rate that would be required when using a similar composition differing only in lacking said secondary alcohol surfactant.

24. A method of controlling unwanted vegetation comprising the steps of:

(a) dissolving or diluting in water in a spray tank a composition of claim 12 to form a spray solution; and (b) applying the spray solution by spraying to the foliage of said vegetation;

said method giving acceptable control in the absence of rain and control which is not unacceptably reduced if rain falls shortly after application.

25. A method for enhancing the rainfastness of a glyphosate herbicide composition, comprising adding to a glyphosate composition a secondary alcohol surfactant having the representative chemical structure

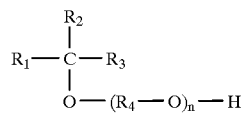

wherein $R_1$ and $R_2$ are independently straight or branched chain $C_1$ to about $C_{28}$ alkyl, aryl or alkylaryl groups and the total number of carbon atoms in $R_1$ and $R_2$ is about 7 to about 30, $R_3$ is hydrogen, $R_4$ groups are independently $C_1$ to $C_4$ alkylene groups and n is an average number from about 3 to about 30, and thereafter applying the composition to unwanted vegetation prior to the onset of rain which would reduce the herbicidal efficacy of a glyphosate composition lacking the secondary alcohol.

26. The method of claim 25 wherein, in the structure of said alcohol surfactant, $R_1$ and $R_2$ are both straight chain alkyl groups with a total of about 7 to about 30 carbon atoms, and $R_4$ groups are ethylene.

27. The method of claim 26 wherein, in the structure of said alcohol surfactant, n is an average number from about 7 to about 14.

28. The method of claim 26 wherein, in the structure of said alcohol surfactant, n is an average number from about 9 to about 12.

29. The method of claim 15 wherein said alcohol surfactant comprises a $C_{11-15}$ unbranched alkyl chain with an ethoxylated alcohol group at any position on the chain except at either end, and n is an average number from about 9 to about 12.

30. The method of claim 15 wherein said alcohol surfactant is added to the spray solution at a concentration of about 0.05 to about 2 per cent by volume.

31. The method of claim 15 wherein said alcohol surfactant is added to the spray solution at a concentration of about 0.1 to about 1 per cent by volume.

* * * * *

UNITED STATES PATENT AND TRADEMARK OFFICE
CERTIFICATE OF CORRECTION

PATENT NO.    : 5,912,209
DATED         : June 15, 1999
INVENTOR(S)   : James W. Kassebaum, Joseph J. Sandbrink and James M. Warner It is certified that error appears in the above-identified patent and that said Letters Patent is hereby corrected as shown below:

In the Claims:
Claim 20, in the structure at line 20, delete "$R_3$" and insert therefor --H--.

Signed and Sealed this

Twelfth Day of June, 2001

*Attest:*

*Attesting Officer*

NICHOLAS P. GODICI
*Acting Director of the United States Patent and Trademark Office*